United States Patent [19]
Christenson

[11] 4,102,979
[45] Jul. 25, 1978

[54] RADIOIMMUNOASSAY FOR BENZOYLECGONINE

[75] Inventor: James Gordon Christenson, North Caldwell, N.J.

[73] Assignee: Hoffmann-La Roche Inc., Nutley, N.J.

[21] Appl. No.: 725,912

[22] Filed: Sep. 22, 1976

[51] Int. Cl.$^2$ ............................ A61K 43/00; G01N 33/16
[52] U.S. Cl. .................................. 424/1; 23/230 B; 424/12; 260/292
[58] Field of Search .................. 260/292; 23/230 B; 424/1, 1.5, 12

[56] References Cited

U.S. PATENT DOCUMENTS

| | | | |
|---|---|---|---|
| 3,498,989 | 3/1970 | Sallay | 260/292 |
| 3,555,143 | 1/1971 | Axen et al | 424/1 |
| 3,709,868 | 1/1973 | Spector | 424/12 |
| 3,888,866 | 6/1975 | Leute et al | 260/292 |
| 3,917,582 | 11/1975 | Soffer et al | 260/292 |
| 3,952,091 | 4/1976 | Grunberg et al | 23/230 B |
| 3,966,744 | 6/1976 | Goldstein et al | 260/292 |

Primary Examiner—Benjamin R. Padgett
Assistant Examiner—Christine M. Nucker
Attorney, Agent, or Firm—Samuel L. Welt; George M. Gould; George M. Gould

[57] ABSTRACT

A radioimmunoassay for cocaine and the cocaine metabolite benzoylecgonine is described. The assay utilizes a novel labelled compound $^{125}$I-4-hydroxybenzoylecgonine.

5 Claims, No Drawings

RADIOIMMUNOASSAY FOR BENZOYLECGONINE

BACKGROUND OF THE INVENTION

Immunoassays for benzoylecgonine are described in U.S. Pat. No. 3,888,866, issued June 10, 1975. The immunoassays disclosed in the patent involve the use of either a stable free radical detector (the FRAT technique) or the use of enzymes as detector moieties (EMIT). A further disclosure to such immunoassays for benzoylecgonine is found in U.S. Pat. No. 3,690,834, issued Sept. 12, 1972.

DESCRIPTION OF THE INVENTION

The present invention relates to a radioimmunoassay for cocaine and benzoylecgonine which assay is of substantially higher sensitivity than previously employed immunoassays for this cocaine metabolite.

The assay of this invention utilizes antibodies specific for cocaine and benzoylecgonine. Such antibodies may be elicited using host animals in a manner known per se employing an antigen wherein benzoylecgonine is the hapten covalently linked to an immunogenic carrier material.

As used herein, the term "immunogenic carrier material" is meant to include those materials which have the property of independently eliciting an immunogenic response in a host animal and which can be covalently coupled to the above described hapten. Suitable carrier materials include, for example, proteins; natural or synthetic polymeric compounds such as polypeptides, e.g., polylysine or copolymers of amino acids; polysaccharides; and the like. Particularly preferred carrier materials are proteins and polypeptides; especially proteins.

The identity of the protein material utilized in the preparation of an antigen of the instant invention is not critical. Examples of suitable proteins useful in the practice of this invention include mammalian serum proteins such as, for example, human gamma globulin, human serum albumin, bovine serum albumin, methylated bovine serum albumin, rabbit serum albumin, and bovine gamma globulin. Other suitable protein products will be suggested to one skilled in the art. It is generally preferred but not necessary that proteins be utilized which are foreign to the animal hosts in which the resulting antigen will be employed.

The covalent coupling of the hapten to the immunogenic carrier material can be carried out in a manner well known in the art. For example, the hapten can be converted to an isolatable activated form prior to coupling. Suitable activated forms include the N-hydroxysuccinimide ester, p-nitrophenyl ester; acylimidazoles; and so forth. Other methods for coupling may be employed wherein the activated intermediates need not be isolated. Such methods include the mixed anhydride method, use of EEDQ (N-ethoxycarbonyl-2-ethoxy-1,2-dihydroquinoline) as coupling agent and the like.

The coupling of the hapten either as the free acid or as an activated derivative to the immunogenic carrier material can be readily accomplished utilizing techniques well known in the art for establishing amide bonds. Thus, for example, one such technique would involve dissolving the carrier material and a coupling agent in a suitable inert solvent followed by adding the hapten. The reaction may be conducted in a temperature in the range of from about 0° C to about 50° C although higher or lower temperatures might be employed depending on the nature of the reactants. A most preferable temperature is about room temperature.

The coupling agent which may be used in the aforesaid reaction will be selected from those commonly employed in organic chemistry for initiating amide bond formation. A particularly suitable group of coupling agents comprise the carbodiimides, most preferably dicyclohexylcarbodiimide or 1-ethyl-3-(3-dimethylaminopropyl) carbodiimide. The molar ratio of the hapten to the carrier material will, of course, depend on the identity of the hapten utilized and the protein selected for the reaction.

Conventional conditions for the coupling reaction can be employed. Thus when utilizing carbodiimides as coupling agents, it is desirable to utilize a slightly acidic reaction medium for this step, e.g., a medium having a pH in the range of from about 3 to 6.5, most preferably in the range of from about 4 to 6.5. Upon completion of the reaction, the excess hapten molecules may be removed by dialysis.

As indicated previously, one technique for preparing the antigens of the present invention is to first prepare and isolate an activated derivative and then to react this compound with the carrier material to form the antigen. Such activated derivatives are conveniently prepared by reacting benzoylecgonine with a desired activating compound, such as N-hydroxysuccinimide, and a coupling agent, such as dicyclohexylcarbodiimide, in an inert solvent. The reaction is usually allowed to proceed for 16-60 hours at reduced temperatures (0°-5° C). The activated derivative may then be isolated by filtering off the by-product, dicyclohexylurea, and distilling off the solvent.

The hapten may then be coupled to the carrier material by contacting the activated derivative with the chosen carrier material. When the activated derivative is the N-hydroxysuccinimide ester and the carrier material is bovine serum albumin, this may be accomplished by adding the activated derivative in a water-miscible solvent to an aqueous solution of the carrier material containing a base, such as sodium bicarbonate.

Another method of coupling carrier protein to hapten is by activating the carboxyl group of the hapten without isolation of an intermediate and adding the activated hapten to the carrier protein. An example of such a reaction is the mixed anhydride obtained by reaction with isobutylchloroformate. The hapten is dissolved in an anhydrous, water-miscible organic solvent, such as dioxane or 1-methyl-2-pyrrolidinone, and the solution is neutralized with an equimolar quantity of triethylamine. After stirring at room temperature, the temperature of the mixture is reduced to between 0° and 8° C. An equimolar quantity plus 10% excess of isobutylchloroformate is then added and stirring is continued. Meanwhile, the carrier protein, e.g., bovine serum albumin, is dissolved in water and the pH is adjusted to 9.0 with NaOH. The quantity of carrier used is approximately equivalent to the molar quantity of hapten divided by the theoretical number of reactive groups on the carrier. Organic solvent is added to the carrier solution and the solution is cooled to between 0° and 8° C. The solution is then added to the activated hapten and coupling is allowed to proceed for 30 minutes to overnight.

The mixture is then dialyzed and the antigen recovered from the dialysis bag.

The antigens of the present invention may be utilized to induce formation of antibodies specific to benzoylecgonine and related compounds in host animals by injecting the antigen in such a host, preferably using an adjuvant. Improved titers can be obtained by repeated injections over a period of time. Suitable host animals for this purpose include mammals such as rabbits, horses, goats, guinea pigs, rats, cows, sheep, etc. The resulting antisera will contain antibodies which will selectively complex with benzoylecgonine or an antigen prepared therefrom, as described above.

The specific antibodies of the present invention are useful as reagents for the determination of cocaine and benzoylecgonine. In such an assay, a known amount of a labeled ecgonine derivative, such as the 4-hydroxybenzoyl ester of ecgonine labeled with $^{125}$I or benzoylecgonine-$^{3}$H is mixed with the above antibody and a sample containing some benzoylecgonine is added. The amount of benzoylecgonine in the sample can be determined by measuring the inhibition of the binding to the specific antibody of the labeled ecgonine derivative by the unknown sample and comprising such value to a standard curve obtained by utilizing known amounts of benzoylecgonine and determining the inhibition of binding for each such amount. In addition a standard curve for cocaine can be obtained by utilizing known amounts of this compound with the antibody-labeled antigen mixture. The reagents may be added in any order. A suitable assay procedure for this purpose is described in greater detail in U.S. Pat. No. 3,709,868.

The novel antigens and antibodies of the present invention may be utilized in conjunction with conventional additives, buffers, stabilizers, diluents, or in combination with other physiologically active substances. The preparation and use of compositions containing antigens or antibodies in conjunction with physiologically acceptable adjuvants is now well known in the art.

EXAMPLE 1

Bovine serum albumin (BSA) conjugate of benzoylecgonine.

1-Methyl-2-pyrrolidinone (NMP; practical grade) was redistilled under reduced pressure (b.p. 78°-80° C at 10 mm Hg). Just before coupling, the solvent was dried by passing it over a column of aluminum oxide (Woelm neutral, activity grade 1). Benzoylecgonine was dried overnight in vacuo over anhydrous calcium sulfate.

A solution of 280 mg of BSA ("crystallized"; 4.1 × $10^{-3}$ mmole) in 8 ml of water was brought to pH 9.0 by the addition of a few drops of 1N sodium hydroxide. To this solution was added 12 ml of NMP and the solution was chilled in an ice bath. Next, 115.7 mg (0.40 mmole) of benzoylecgonine was dissolved in 8 ml of dry NMP with gentle warming and this solution was also chilled in an ice bath. To the chilled benzoylecgonine solution was added and mixed 0.61 ml of a solution of one volume of triethylamine in nine volumes of dry NMP (0.44 mmole of triethylamine). Then 0.53 ml of a solution of one volume of isobutylchloroformate (Eastman) in nine volumes of dry NMP (0.40 mmole of isobutylchloroformate) was added and mixed well. The solution was returned to the ice bath and allowed to stand for 20 minutes, during which time a precipitate appeared, suspended throughout the mixture. This activated benzoylecgonine solution was then added, precipitate and all, to the BSA solution, dropwise and with magnetic stirring in an ice bath. The clear solution was allowed to stand at 4° C overnight.

The solution was then transferred to a dialysis bag (Spectrapor No. 2) and dialyzed against 200 ml of NMP-water (1:1, v/v) for 6 hours at 4° C. The dialysate was changed and dialysis was continued overnight. The solution was then dialyzed against three changes of 1 l of phosphate buffered saline over about 30 hours.

After antibodies had been obtained, the degree of coupling of the hapten could be estimated by radioimmunoassay. In one such preparation, for example, this was found to be approximately 25 moles of hapten per mole of BSA.

EXAMPLE 2

Immunization and bledding. — For immunization of goats and rabbits, the dialyzed material was diluted with phosphate buffered saline to a protein concentration of approximately 2 mg/ml. The diluted immunogen was then emulsified with an equal volume of Freund's adjuvant. The first three inoculations (using complete adjuvant) were administered at weekly intervals, the fourth after another three weeks, and monthly thereafter (the fourth and successive inoculations used incomplete adjuvant). Each inoculation comprised two subcutaneous injections of 0.5 ml each. Test bleedings were taken at 2, 3, and 4 weeks after the first inoculation. After 5 weeks, and at biweekly intervals thereafter, larger quantities of blood were drawn and serum prepared by standard techniques. Thus when rabbits were utilized about 50 ml. was drawn while for goats about 300 ml. of blood was drawn.

EXAMPLE 3

Preparation of $^{125}$I-labeled 4-hydroxybenzoylecgonine. — 4-Hydroxybenzoylecgonine was dissolved in water to a concentration of 1 mg/ml. This solution was then used for iodination with $^{125}$I by the chloramine-T method using Na$^{125}$I. The labeled antigen was purified by chromatography on a 1.5 × 90 cm column of Bio-Gel P-2 (Bio-Rad Laboratories). Good results are obtained if care is taken in the selection of fractions to be saved.

The labeled antigen can also be purified on a 0.8 × 12 cm column of QAE-Sephadex A-25 (Pharmacia Fine Chemicals). The product elutes in a symmetrical peak after about 50 ml of 0.1 M Tris buffer, pH 7.0, and shows excellent antibody-binding properties. For this reason the ion-exchange purification is preferred.

EXAMPLE 4

Assay procedure. — The assay procedure is similar to that used in other ABUSCREEN ® radioimmunoassays. The sample volume required for the assay is 0.1 ml. For quantitative evaluation, standard curves are prepared by plotting the radioactivity in the supernatant, following ammonium sulfate precipitation, against the logarithm of concentration for 1000, 250, 100, 50, 25, 10 and 5 ng/ml solutions of benzoylecgonine in normal human urine.

Performance of the assy. — Standard solutions were prepared by diluting a 1 mg/ml solution of benzoylecgonine to the required concentration with normal human urine. Such standard solutions were used to prepare a standard curve. The assay can readily detect benzoylecgonine at concentrations well below 100 ng/ml (10 ng in 0.1 ml of urine). This is more sensitive than the most sensitive thin layer and gas-liquid chromatographic methods that have been published (Wallace et al., J. Chromatogr., 114, 433 (1975); Wallace et al., Anal. Chem. 48, 34 (1976). It is also considerably more sensitive than the commercial EMIT (enzyme multiplied immunoassay technique) assay for benzoylecgonine, which has a "cut-off" level of $\mu g/ml$ or the FRAT (free radical assay technique) which has a "cut-off" of 0.5 $\mu g/ml$.

A population of 100 normal urine specimens was tested to determine the range of normal values with the following results;

Table I

| Range of Benzoyledgonine Equivalents (ng/ml) | Number of Urines |
|---|---|
| 0 | 29 |
| 1 to 5 | 65 |
| 6 to 10 | 5 |
| 10 | 1 (11 ng/ml) |

Thus, a cut-off level of 100 ng/ml provides a generous margin against falsely positive results.

As is the case in most radioimmunoassays, the assay is not absolutely specific for benzoylecgonine. The only significantly cross-reacting compounds which have been identified are cocaine congeners, however, so the clinical utility of the assay is not diminished by its cross-reactivity. The cross-reactivity properties of the antiserum apparently vary somewhat from lot to lot. A summary of cross-reactivity data which have been obtained with the best studied lot are shown in Table II. Note that cocaine is almost as reactive as benzoylecgonine and thus the antibody can be used to assay for cocaine, while ecgonine is approximately 200-fold less reactive. Scopolamine, atropine, and procaine gave negligible responses (a neglible response is defined as a response of less than 100 ng/ml of benzoylecgonine equivalents at a test drug concentration of 100 $\mu g/ml$, i.e., a relative reactivity less than $1 \times 10^{-3}$).

Some cross-reactivity was observed with the phenothiazine derivatives, thioridazine, chlorpromazine, and trifluoperazine but these responses were negligible as defined above.

TABLE II

| Compound | Structure | Relative Reactivity* |
|---|---|---|
| Cocaine | 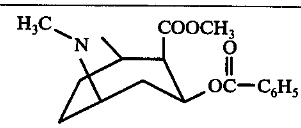 | 0.77 |
| Tropacocaine | 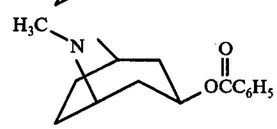 | $1.2 \times 10^{-2}$ |
| Ecgonine | 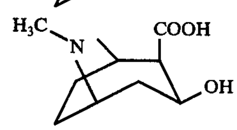 | $4.9 \times 10^{-3}$ |
| Scopolamine | 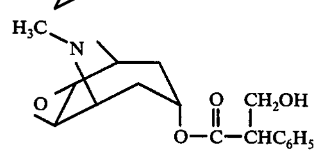 | NR** |
| Atropine | 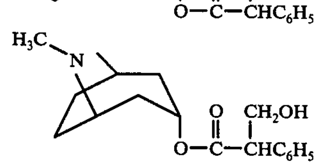 | NR |
| Tropine | 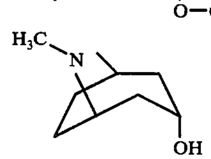 | NR |
| Tropinone | 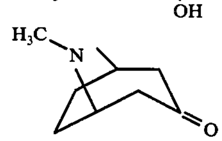 | NR |
| Tropine-N-oxide | 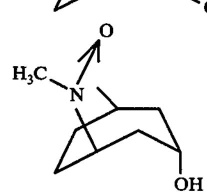 | NR |

TABLE II-continued

| Compound | Structure | Relative Reactivity* |
|----------|-----------|----------------------|
| Procaine | 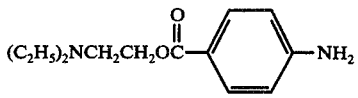 | NR |

*Relative reactivity is defined as the ratio of benzoylecgonine concentration to test drug concentration for a given response.
**NR = negligible response (defined in text).

EXAMPLE 5

Ecgonine methyl ester (p-acetoxy) benzoate hydrochloride.

Under nitrogen, in a 250 ml flask, were placed 3.21 g (0.016 mole) of ecgonine methyl ester, 115 ml of dry benzene, 3.5 g p-acetoxybenzoyl chloride and 24.7 ml triethylamine. After 18 hr reflux, the mixture was cooled to room temperature, filtered, and washed with benzene, and the filtrate concentrated at reduced pressure to an oil. Treatment of the residual oil with ethereal hydrogen chloride afforded 5 g of product, mp 150° Cd., 78.2% of theory.

EXAMPLE 6

Ecgonine, 4-hydroxybenzoic acid ester, hydrochloride, hemi hydrate, hemiethanolate.

Under nitrogen 4.3 g of ecgonine methyl ester (p-acetoxy) benzoate was refluxed with 125 ml of water for a period of 18 hours. The cooled solution was made alkaline with sodium carbonate, and extracted with 4×25 ml portions of chloroform. The aqueous solution was then acidified with concentrated hydrochloric acid to pH 6.5 followed by extraction with 7×30 ml portions of chloroform. The aqueous solution was then made acid to pH 2 with concentrated hydrochloric acid, and concentrated to dryness. The residue was slurried in methanol and filtered. Concentration of the methanol filtrate gave 3.1 g of solid which was crystallized from ethanol. The yield of product was 0.85 g, mp 180°–181° Cd.
$[\alpha]_D^{25} = -72.0°$ (c = 1, methanol).

EXAMPLE 7 o-Iodobenzoylecgonine.

A solution of ecgonine (185 mg, 1 mmol) in aqueous acetone (1.5 ml $H_2O$ + 4.5 ml acetone) was stirred for 4½ days at room temperature with o-iodobenzoic anhydride (1.43 g, 3 mmol). Evaporation of the solvent in vacuo and tritiaration of the residue with hexane-ether (1:1, to remove the iodobenzoic acid) gave a solid which after being dissolved in methanol and purified by preparative thin layer chromatography (silica gel, 2 mm; ethyl acetate, acetic acid, water 4:4:1) gave 120 mg of o-iodobenzoylecgonine. M.p. 183°–185° C. Nmr and ms data are in agreement with structure.

EXAMPLE 8 o-Benzoylecgonine-$^3H$ o-Iodobenzoylecgonine (15 mg, 0.036 mmol) and triethylamine (4.9 ul, 3.64 mg, 0.036 mmol) were dissolved in 0.5 ml of dry methanol in a system having a capacity of 3.5 ml. 10% Palladium on carbon catalyst (5 mg) was added. After evacuation, approximately 2 curies of carrier free tritium gas were admitted (0.036 mmol, about 0.73 ml) and the system was first isolated, then stirred at room temperature 1 hour. Any unreacted tritium gas was then removed and 1 ml of methanol was added. The catalyst was filtered off and the filtrate concentrated to dryness in vacuo. Four such concentrations (to remove labile activity), from 1 ml of methanol each, gave a white residue which was purified by preparative thin layer chromatography (silica gel, 5% ammonium hydroxide in methanol). 4.1 mg (85.27 mCi) of product were isolated having a specific activity of 20.80 mCi/mg (6.01 mCi/mmol) and a radio chemical purity of < 99% (tlc: silica gel; methanol).

EXAMPLE 9

O-Benzoylecgonine-$^2H$

The procedure of Example 8 was carried out with deuterium gas and gave product which contained 93.7% $d_1$, and 6.3% do (mass spec. and nmr).

I claim:

1. A method for the radioimmunoassay of benzoylecgonine and cocaine in a sample, which method comprises mixing said sample with a known amount of a radiolabeled benzoylecgonine compound selected from the group consisting of benzoylecgonine - $^3H$ having a specific activity suitable for radioimmunoassay procedures and $^{125}I$-4-hydroxybenzoylecgonine thereof and an antibody which will selectively complex with said benzoylecgonine or cocaine, measuring the degree of binding of said radio-labeled benzoylecgonine compound, and determining the amount of benzoylecgonine and cocaine present in said sample by comparing said degree of binding to a standard curve obtained by mixing known amounts of benzoylecgonine or cocaine with fixed amounts of labeled benzoylecgonine compound and said antibody and determining the degree of binding for each known amount of said benzoylecgonine or cocaine.

2. The method of claim 1 wherein radiolabeled benzoylecgonine compound is 4-hydroxybenzoylecgonine.

3. The method of claim 1 wherein the radiolabelled benzoylecgonine compound is benzoylecgonine-$^3H$ having a specific activity suitable for radioimmunoassay procedures.

4. The method of claim 1 wherein said radioimmunoassay is for benzoylecgonine.

5. $^{125}I$-4-hydroxybenzoylecgonine.

* * * * *

UNITED STATES PATENT AND TRADEMARK OFFICE
CERTIFICATE OF CORRECTION

PATENT NO. : 4,102,979
DATED : July 25, 1978
INVENTOR(S) : James Gordon Christenson It is certified that error appears in the above—identified patent and that said Letters Patent is hereby corrected as shown below:

Column 8, line 43, claim 1 "thereof" should be deleted.

Column 8, line 55, claim 2 after "wherein" should read said .

Signed and Sealed this

Thirteenth Day of May 1980

[SEAL]

Attest:

SIDNEY A. DIAMOND

*Attesting Officer*  *Commissioner of Patents and Trademarks*